United States Patent [19]

Calderon

[11] Patent Number: 4,883,459
[45] Date of Patent: Nov. 28, 1989

[54] RETROGRADE PERFUSION

[76] Inventor: Reynaldo Calderon, 5620 Greenbriar #105, Houston, Tex. 77005

[21] Appl. No.: 139,065

[22] Filed: Dec. 21, 1987

Related U.S. Application Data

[63] Continuation-in-part of Ser. No. 83,673, Aug. 12, 1987, Continuation-in-part of Ser. No. 871,528, Jun. 6, 1986, Pat. No. 4,714,460, Continuation of Ser. No. 518,685, Jul. 29, 1983, abandoned.

[51] Int. Cl.$^4$ .............................................. A61M 1/00
[52] U.S. Cl. ................................. 604/28; 128/656; 600/4; 604/35; 604/101; 604/118
[58] Field of Search ............ 128/328, 334 R, 654–656, 128/658, 804; 604/4, 8, 9, 27, 28, 35, 38, 40, 41, 43, 49, 52, 53, 93, 96, 101, 118, 121, 151, 264, 284; 600/1–4, 9, 10

[56] References Cited

U.S. PATENT DOCUMENTS

| | | | |
|---|---|---|---|
| 2,854,982 | 10/1958 | Pagano ................................. | 604/101 |
| 3,888,239 | 6/1975 | Rubinstein ........................... | 128/655 |
| 4,192,302 | 3/1980 | Boddie .............................. | 128/DIG. 3 |
| 4,445,892 | 5/1984 | Hussein et al. ....................... | 604/101 |
| 4,709,703 | 12/1987 | Lazarow et al. ...................... | 128/654 |
| 4,714,460 | 12/1987 | Calderon ............................... | 604/28 |
| 4,908,718 | 11/1987 | Daniels ................................. | 604/53 |

FOREIGN PATENT DOCUMENTS 0651817  3/1979  U.S.S.R. .................................. 604/48

OTHER PUBLICATIONS

Folkman, J., "The Vascularization of Tumors", p. 59–73.
Kato, T., "Arterial Chemoembolization with Microencapsulated Anticancer Drug", The Journal of the American Medical Association, 3/20/81, pp. 1123–1127.

Primary Examiner—C. Fred Rosenbaum
Assistant Examiner—Mario Costantino
Attorney, Agent, or Firm—Pravel, Gambrell, Hewitt, Kimball & Krieger

[57] ABSTRACT

Tumors in the body of a patient are studied in situ by a monitor, such as computer assisted tomography, X-ray or the like, while optimal flow paths through the tumor area are established. A catheter with a suction lumen and an infusion lumen, with seals associated with each, is placed in the patient's vein near the tumor. Flow is then sealed in the vein with the infusion seal. A carrier medium dye is injected into the tumor at selected flow rates and differential pressures. Flow of the dye through the tumor is observed on the monitor to determine optimal retrograde perfusion paths through the tumor for the selected flow rates and differential pressures. Once the optimal perfusion paths are noted, a preferential attack area in the tumor is located using a different, less dense carrier dye and increased fluid back pressure in the infusion system. Once the attack area in the tumor is located, microspheres with active ingredients, such as chemotherapy, can be selectively perfused through one of the paths in the tumor to the attack site and forced into the tumor, once at the attack site, using increased back pressure. The process may be cyclically repeated using the same or different active ingredients. The procedure may be repeated through the tumor in different paths and attack points at desired active ingredient dosages using increased back pressures.

11 Claims, 6 Drawing Sheets

RETROGRADE PERFUSION

CROSS-REFERENCE TO RELATED APPLICATIONS

The present application is a continuation-in-part application of applicant's co-pending U.S. Pat. application Ser. No. 83,673, filed Aug. 12, 1987 and of co-pending U.S. Pat. application Ser. No. 871,528 filed June 6, 1986 now U.S. Pat. No. 4,714,460 dated Dec. 22, 1987, which is a continuation of U.S. patent application Ser. No. 518,685, filed July 29, 1983, now abandoned.

Background of Invention

1. Field of Invention

The present invention relates to treatment of tumors.

2. Description of Prior Art

In the conventional treatment of a solid tumor, the state of the art lies in arterial infusion, a one-way process which comprises a single pass of a chemotherapeutic agent via the arterial side of the body through the tumor. The principal drawback to this method is the inability to maintain the dose rate and/or duration of exposure of a drug necessary to effect a response, due to the resulting systemic toxicity. That is, with present methods, the successful treatment of a solid tumor with chemotherapy is undermined by leakage of the chemotherapy which proves detrimental to the remainder of the body.

Routine blood flow originates in the heart and progresses in an arterial to capillary to venous sequence. The walls of the post-capillary venules, capillaries, and sinusoids are exchange vessels, serving as the site of exchange between the blood and the tissue bathing the cells. The larger venules and veins comprise a system of capacitance or reservoir vessels. These are large-volume, low-pressure vessels through which the cardiac (right side of the heart) return occurs.

Under normal conditions, the endothelial cells that form the lining of the vascular network renew themselves very slowly. According to Folkman, in an article entitled "The Vascularization Of Tumors," *Scientific American*, June 1976 (p.71), "Occasionally there is a brief burst of proliferative activity in one part of the vascular system when such activity is needed to heal a wound or mount an immune response. However, the new vessels always regress after a short time, and regenerative activity subsides to its former low state." The cells proliferate rapidly where needed for the purpose of immunity as of healing wounds. However, such proliferation is maintained only as long as necessary. Thereafter, regenerative activity resumes its former state.

Blood circulation to a solid tumor likewise flows routinely from arterial to capillary to venous. However, in the topographical region between the exchange vessels and the larger venules, the direction of flow changes dramatically. Folkman explains what occurs: "When a malignant tumor sends out its chemical message, the proliferation of endothelial cells rises steeply in the vicinity of the tumor. Capillaries bud from the side walls of venules and lengthen into thin tubes, converging on the tumor from all directions." This characteristic of the tumor vessels results in the creation of numerous venous—venous (V—V) shunts, which are the physical elements that underlie the process of retrograde perfusion. The significance of the V—V shunts in the treatment of tumors is explained as follows.

The normal driving pressure in the tumor vasculature is the change in velocity of the blood flowing from the capillary into the venous system by means of the cross-sectional area ($V \times A_{capillaries} = V \times A_{venous}$). That is, the pressure drop across these V—V channels is created by the change in velocity of the blood flow as it emerges from the capillaries. The tumor blood flow is thus impaired, measuring only two to fifteen percent of that of the surrounding tissue, and this impaired circulation distinguishes the cancer vasculature. The probability of blood flow through the V—V shunts is far less than the probability of blood flow through the normal vasculature. Therefore, in any attempt to deliver chemotherapy to a tumor, the likelihood that the drug will spread to the remainder of the body is far greater than the likelihood that it will reach the tumor.

Systemic toxicity resulting from chemotherapeutic regimens remains an obstacle to the successful treatment of cancer. In 1961, Stehlin, et al. identified leakage of the chemotherapeutic agent into the systemic circulation as "one of the most serious limitations as to the success of perfusion of certain regions of the body." As recently as March, 1981, the *Journal of the American Medical Association* featured an article by Kato, et al. and a related editorial by Chuang addressing chemoembolization, which is the "combination of arterial infusion of a chemotherapeutic agent and arterial embolization of the vascular supply to a neoplasm." This method produced a prolonged survival rate; however, the dosage rate was limited by systemic toxic effects. Similarly, in all of the techniques outlined by Fewer, Wilson and Lewis, the outflow returning to the venous system was left unaltered, resulting in systemic toxicity and a failure to maintain the needed duration of exposure of the drug. Dosage rate is another critical factor in cancer chemotherapy. Evidence supports the conclusion that maintenance of high doses of anti-tumor therapy substantially increases the response rate. This can be noted in marrow transplants, isolation infusion, or regional perfusion studies. Yet, arterial perfusion and infusion into the solid mass tumors have demonstrated that the first passage of the drug in those methods is the only advantage over intravenous (IV) injection; thereafter toxicity remains the same.

SUMMARY OF THE INVENTION

Briefly, the present invention provides a new and improved method and apparatus for treating a tumor in the body of a patient with a chemotherapeutic agent. It is done by retrograde perfusion of the type described and disclosed in Applicant's prior co-pending U.S. patent applications Ser. Nos. 871,528, now U.S. Pat. No. 4,714,460 dated Dec. 22, 1987 and 83,673, referenced above.

The present invention is illustratively described as comprising a two catheter lumen with extensive maneuverability along with at least two controlled injectors as well as pumps, filters, analyzers, and other suitable means for regulating and monitoring the outflow draining from the tumor. The initial step is to take a number of arteriograms which yield graphic representations of the internal loops within the blood flow of a tumorous organ which is to be treated. This aids in determining the preferential drainage, in effect forming a library or map of flow paths. The process begins with retrograde insertion of a catheter with lumens into the preferential drainage of a solid tumor via an external vein. The catheter has a suction lumen and an infusion lumen extending beyond the suction lumen and is located in a vein of a patient near the tumor. An infusion seal is located on the catheter between the infusion lumen and the suction lumen, while a suction seal is located on the catheter to seal flow in the patient's vein past the suction lumen. The infusion lumen marks the site of entry of the tracer agent and provides access to the V—V shunt. The second, or suction, lumen, is placed distally and has the suction capacity necessary to accommodate the tracer agent input, the arterial blood flow, the venous and lymphatic drainage, and the preferential drainage. Next, with the catheters in position; retrograde emboli are placed in critical areas of the vasculature to inhibit leakage.

Once the catheter has been determined to be properly placed by a suitable monitor, a carrier medium which is observable on the monitor is injected into the tumor from the infusion lumen. According to the present invention, the carrier medium is injected at selected flow rates and pressures into the tumor and carrier medium progress through the tumor toward the suction lumen noted on the monitor. Preferential flow paths through the tumor which are formed at certain established flow rates and pressures are noted.

After the flow paths are identified, a first tracer fluid such as a radiograph dye or contrast medium is perfused with the two catheter lumen into a selected one of the flow paths and a steady state flow rate and pressure are established. Once this occurs, a suitable amount of second tracer fluid of lesser density than the first is introduced as a plug or batch in place of the first fluid in this infusion system. When the second tracer fluid reaches the site of the tumor the fluid back pressure on the infusion stream is increased. Since the tumor blood vessels are more leaky than normal ones, the second tracer fluid is forced into the interstitial spaces of the tumor, indicating a preferential target site for chemotherapeutic or other treatment of the tumor. The catheter lumens placed within the tumor preferential drainage as described above form a third in-vivo space in addition to the first (cells) and second (interstitial spaces around the cells) in-vivo spaces.

Next either a tracer fluid or an active ingredient, such as a chemotherapeutic agent, is then injected into the tumor at one of the established flow rates and pressures so that the agent follows one of the preferential flow paths. The flow rate and pressure of injection are maintained until a steady state flow rate and pressure are established. After this occurs, a chemotherapeutic agent which is less dense than the fluid flowing at steady state flow rate and pressure is sent as a batch or plug through the tumor.

When the less dense treatment agent reaches the preferential target site, the back pressure in the infusion system is again increased. This forces the treatment agent into the interstitial spaces of the tumor at the preferential target site for treatment. The original fluid is introduced after the treatment agent and the back pressure on the infusion system is reduced once the treatment agent passes beyond the preferred target. This process may be repeated for a number of back pressure change cycles and treatment agent batches.

Once the target site is established, a thermal sensor, such as a thermistor, is stereotaxically guided using fluoroscopy to the target site. Heated fluids may then be introduced into the organ with the infusion system and forced into the tumor with back pressure so that measurements can be taken by the thermal sensor to assess progress of tumor treatment.

Within the selected areas of an organ chosen for perfusion, feedback loops have been formed with exterior access to a monitoring system which monitors pressure, concentration, temperature, time, and other variables to insure that systemic toxicity is avoided, that an appropriate dose rate of a particular one of the range of active ingredients is maintained, and that the integrity of the organ is not violated. As the drug is perfused through the solid tumor, it is bio-transformed responsive to the conditions of at least one and preferably all three of the body, the tumor, and the drug itself. Next, it is led out of the body via the suction catheter to be filtered and analyzed by suitable filter and analyzer means. Then, the process is repeated as often as necessary until the desired steady state is achieved. Retrograde perfusion according to the present invention thus provides a treatment technique which succeeds in effect in establishing the clinician as an element of the tumor vasculature. From this vantage point, the clinician is able to interact with the tumor and see what the possibilities of interaction are, becoming a monitor of the tumor's evolutionary process and thus being capable of disrupting the homeostatic inertia of the tumor, creating a feedback system with virtually unlimited interaction made possible.

A different active ingredient can subsequently be introduced as a plug or batch using back pressure along the same established flow path, or the lumens and emboli moved to other locations in the tumor where flow paths have been noted to be capable of being established. The same or different active ingredients may then be infused through the tumor along the new flow path and the foregoing back pressure procedure repeated. This procedure is continued for each flow path established until treatment is completed.

The present invention is characterized by three features commonly lacking in previous methods of treatment. First, previous methods fail to change the basic pattern of the established blood flow in the tumor. Second, previous methods allow the established cancer cells to persist, never interrupting the homeostatic inertia of the tumor. Finally, because previous methods lack the capability of interacting with the tumor and attacking it at a preferential target site, they are incapable of controlling the flow pattern and thus the target site, duration of exposure, dose rate, preferential drainage, leakage factor, and level of toxicity which are crucial in the successful treatment of cancer.

One advantage of the present method is that it recognizes the significance of the V—V shunt, but no longer treats vascular flow through the V—V shunt as a substrate limited process. The physical structure of the tumor vasculature is a limiting factor in the delivery of chemotherapy. By the nature of their location beyond the pre-capillary sphincter and and the capillary beds, the V—V shunts can be perfused only randomly by present methods—concentration, duration of exposure, in short, bioavailability of chemotherapy is random. With retrograde perfusion it is no longer necessary to reckon with the impaired circulation through the tumor, for the new method will enable the clinician to provide chemotherapy at a pressure rate needed to drive the flow backward through the flow paths created in the tumor vasculature at a chosen site. Because the flow paths are created such that leakage sites are blocked, systemic toxicity is avoided, yet adequate levels of chemotherapy are certain to reach the tumor at a preferred target site.

A second advantage of retrograde perfusion is that it recognizes the importance of tumor progression, which is the steady increase in malignancy characteristic of vascularized tumors. According to Folkman, tumor progression is a result of the rapid increase in cell division cause by vascularization. As cells proliferate over a period of time, they at first metastasize, then invade surrounding tissue, and finally, appear as ascites cells in the host's abdominal cavity. The present method appreciates the different stages of tumor progression and allows the clinician to intervene selectively at the appropriate time and site with the appropriate combination of dose rate, concentration, pressure, duration of exposure, and other factors which will inhibit vascularization with subsequent tumor growth.

The dose response curve of chemotherapeutic agents is well known; the more effective the drug, the steeper the curve. Presently, dose response is measured by three criteria—reduction in tumor mass, increased survival, or bioassay methods. A third advantage of retrograde perfusion is that it permits optimum assessment of the steep dose response curve, particularly by the bioassay method. By closely tracking the dose response, every effort is made to eliminate the deflection point which represents tumor growth and decreased patient survival.

Another advantage of the present method is that it virtually separates the tumor from the body. Division of the tumor load from the host provides opportunities in several ways. It heightens the immune system; it eliminates the single pass of chemotherapy typical of arterial perfusions; it provides constant contact of the chemotherapeutic agent within the tumor vessels, which is particularly useful with a radio-sensitizing agent; and it facilitates delivery of a radioactive slurry via the catheter system. Furthermore, the chemotherapy can be calculated on the basis of tumor burden rather than being limited by the effects of the systemic toxicity, and the concentric catheters can be utilized as an access point for hyperalimentation to induce patient well-being.

DESCRIPTION OF THE PREFERRED EMBODIMENT

Figure 1:
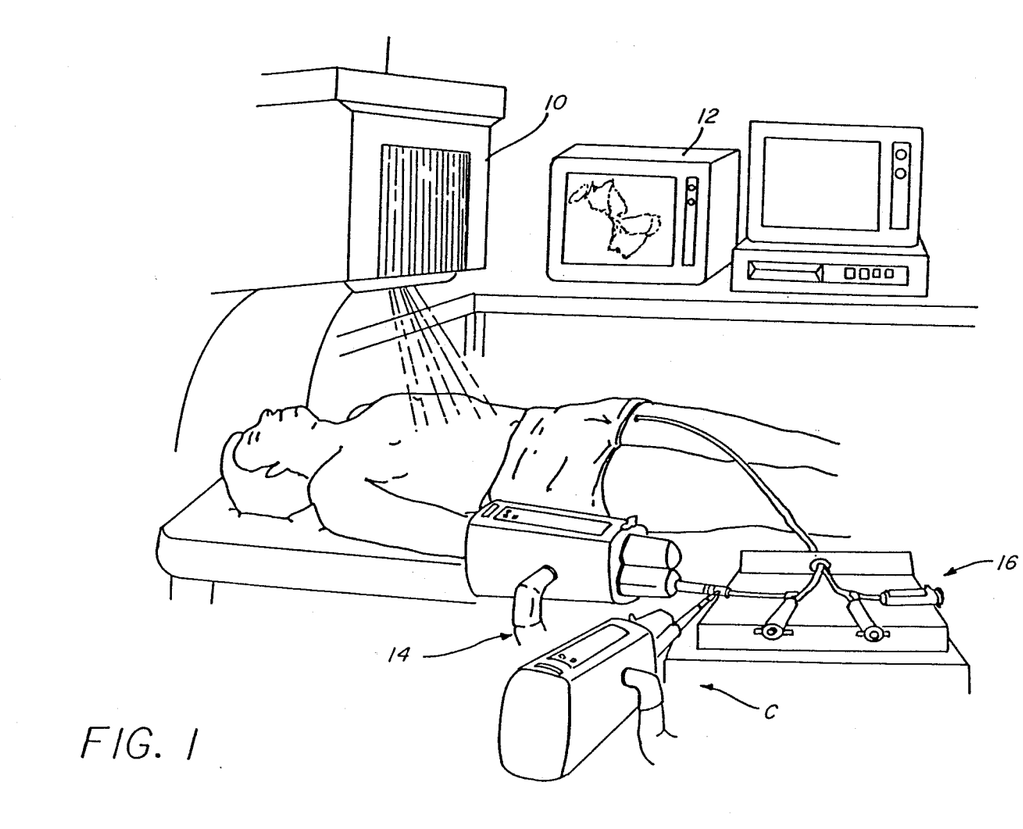
FIG. 1 is an isometric view of a patient undergoing treatment according to the present invention.

According to the present invention, a double balloon concentric catheter system C (FIGS. 1 and 2) is used to treat a person. The catheter C is used for retrograde perfusion of a patient's body, by which is meant that an agent is injected into the patient's venous system in a direction counter to normal blood flow. The retrograde injected agent then perfuses a portion of the body being treated via the venous system.

In a preferred embodiment, the catheter system C is used to inject and retrograde perfuse one or more active ingredients, such as monoclonal antibodies, lymphokines or differentiation factors, through a solid tumor at selected times in such a way that variables, such as the cidal concentration, duration of exposure and systemic toxicity may be controlled. As will be set forth in detail below, the active ingredients may be introduced along the same or different flow paths established through the tumor according to the present invention.

During treatment according to the present invention, the patient's response and reactions are observed and monitored by a monitor, such as computerized axial tomography (CAT) scanner 10 (FIG. 1) and a video monitor 12, using two double balloon concentric catheters 14 and 16. The double balloon concentric catheters 14 and 16 according to the present invention include an inner tube or infusion lumen 18 (FIG. 2) encircled near an end or tip 20 by an infusion seal or inflatable balloon 22 which is used to seal a patient's vein in which the lumen 18 is placed. The catheters 14 and 16 are shown in somewhat simplified form in FIG. 2 in order that structural features may more clearly be seen. The infusion lumen 18 is used on insertion to direct the flow of the therapeutic input fluid through vessels in the portion of the body being treated. As is usual, a guide wire 24 is provided in the end 20 of lumen 18 to assist in insertion and movement to the desired location in the patient's venous system. The guide wire 24 is withdrawn once the lumen 18 is properly positioned.

Figure 2:
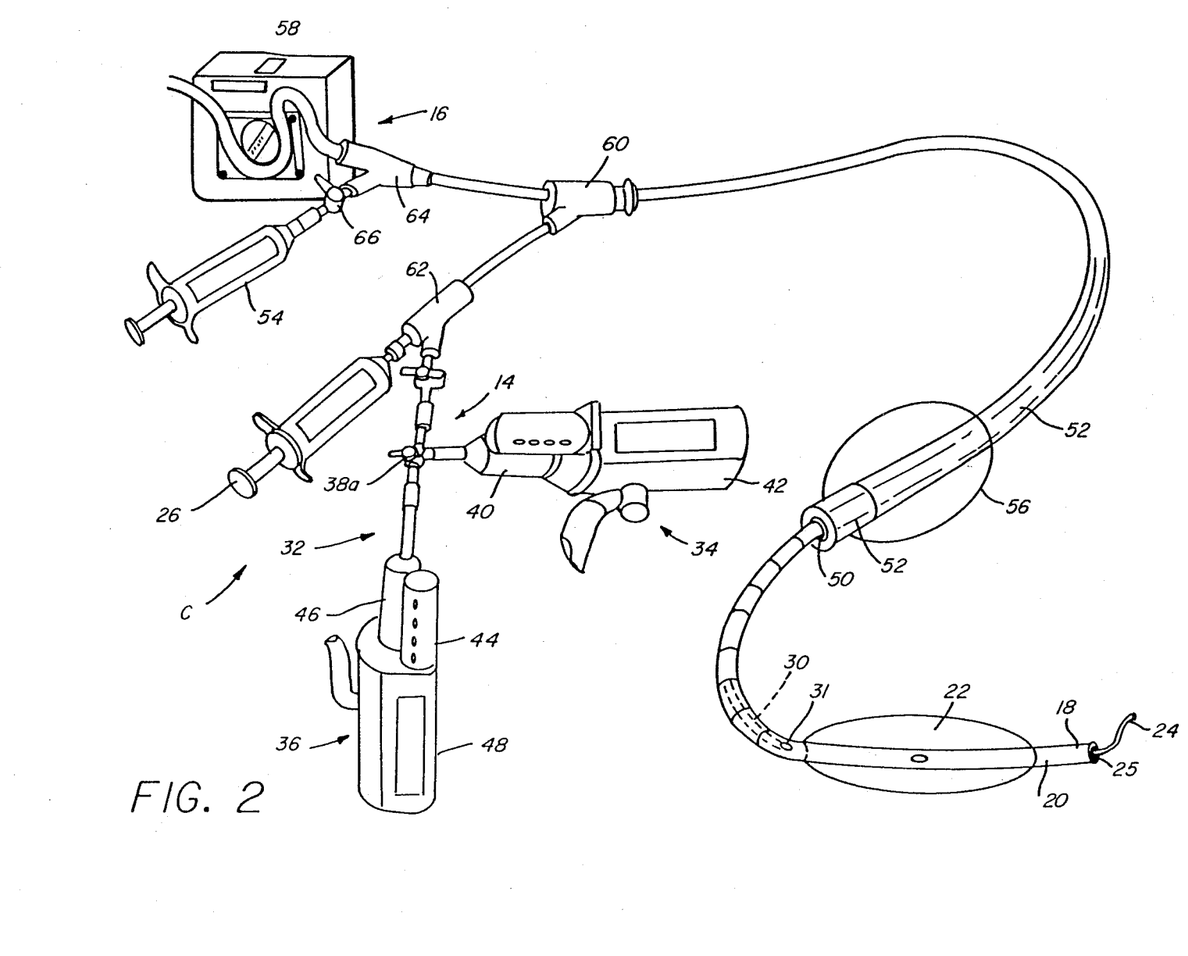
FIG. 2 is a schematic view of an apparatus according to the present invention.

Driving power for the infusion lumen 18 is provided by a syringe injector 26 with push/pull capacity to insert and withdraw the lumen 18 which aids in establishing feedback loops of multiple flow paths beginning in the tumor vessels and extending outside the body. This makes it possible to control the concentration, flow rate, differential pressure, temperature, and time duration of active ingredient input. In this manner systemic toxicity is avoided, appropriate dose rate of selected active ingredients through established flow paths through the tumor are maintained, and the integrity of the organ is not violated. The infusion lumen 18 further includes an opening passage 25 in the end 20, forming a site of entry of either a carrier medium or an active ingredient into the patient's vein. The infusion lumen 18 may have an additional passageway or lumen 30 formed therein which may be used for either infusion or suction purposes. A port is located within an area encircled by the inflatable balloon 22 to allow inflation of the balloon 22 as desired for sealing the veins and directing the flow of fluids. A port 31 may be formed, if desired, in the lumen 18 as an inlet to lumen 30 behind the inflatable balloon 22 to permit injection or extraction of fluid from the patient's vein.

The catheter system 14 further includes an injection system 32 including a flow path injector 34 and treatment injector 36 selectively placed in fluid communication with infusion lumen 18 via valve 38a. The flow path injector 34 includes a container 40 for a suitable carrier medium for injection from container 40, when connected via valve 38a, into the patient's vein via infusion lumen 18. The flow path injector 34 may be, for example, a Model 510 Mark V injection system of the type sold by MEDRAD, Inc. of Pittsburgh, Pa.

The treatment injector 36 includes a first container 44 for either a carrier medium or a first active ingredient of the type set forth above and a second container 46 for a second active ingredient of the type set forth above. The active ingredients in containers 44 and 46 are typically transported on microspheres, and the flow and dosage rate and application pressure into the patient's vein via infusion lumen 18, when connected via valve 38a, is controlled by an injector control 48. The treatment injector 36 may be, for example, a Model 570 Mark V injection system of the type sold by MEDRAD, Inc. of Pittsburgh, Pa.

A port 50 in a suction lumen 52 collects either return carrier medium or partially or wholly spent active ingredient, depending on which is being infused, in a collector syringe 54 after it has been retrograde perfused through the tumor vessels, as hereinafter set forth. The infusion lumen 18 is preferably concentrically mounted in the suction lumen 52 which functions to transport the collected fluids outside the body to collection syringe 54, from which such fluids may be transferred to a suitable filter for filtration purposes. The filtered, toxic-free active ingredient may then be stored or alternatively re-injected into the veins via port 25.

The suction lumen 52 of the present invention also includes a suction seal or balloon 56 which is inflatable in the patient's vein via a port to seal the vein, blocking the flow of infused fluids from the injection lumen 18 to the remainder of the patient's body. A pump 58, such as a unified variable speed drive pump sold under the trademark "MASTERFLEX" by the Cole-Parmer Instrument Co., is provided to selectively control back pressure in the catheter system C, for reasons to be set forth. The pump 58 is also provided with push/pull capacity to insert and withdraw the lumen 52 during establishment and utilization of multiple flow paths through the tumor.

Lumens 18 and 52 are jointed and made common at a T-junction or side arm 60. Similarly, the fluid passage to syringe 26 and injector system 32 branch and remain separate so their fluids do not mix at a side arm 62, while a side arm 64 branches the fluid passages to syringe 54 and pump 58, keeping their respective fluids separate and distinct. The syringe 54 is connected to the side arm 64 by a connecting-Tee 66.

Figure 3:
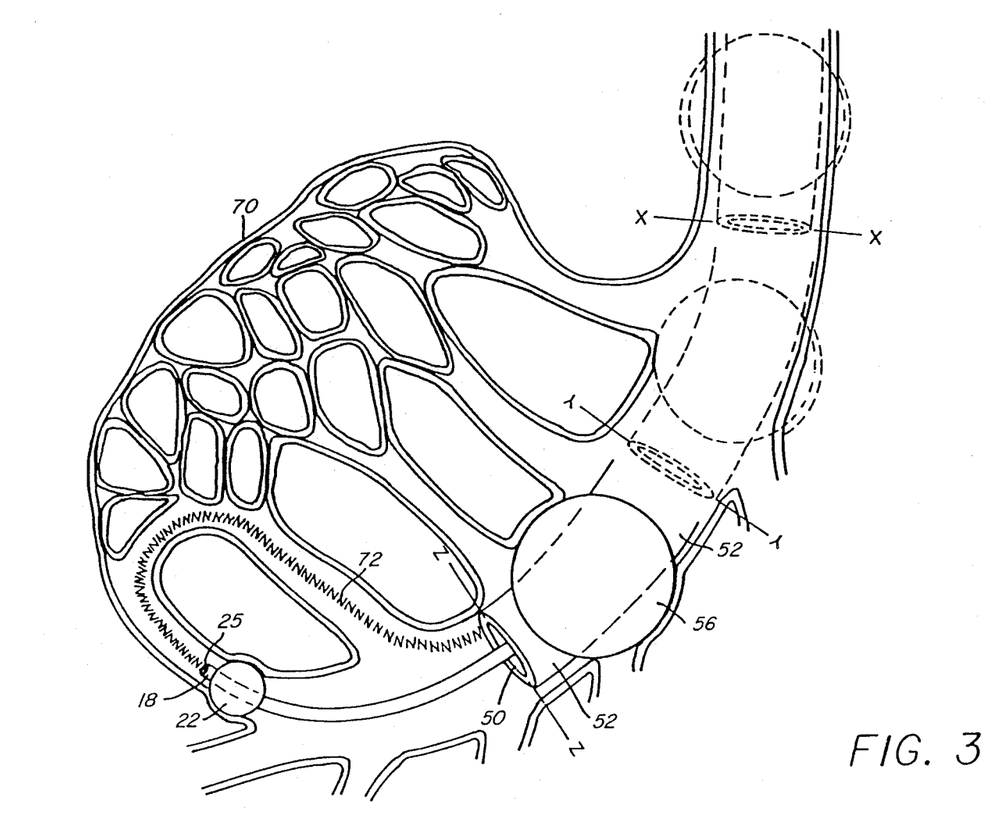
FIGS. 3, 3A, 4, and 4A are enlarged schematic views of body organs being treated according to the present invention.
Figure 3A:
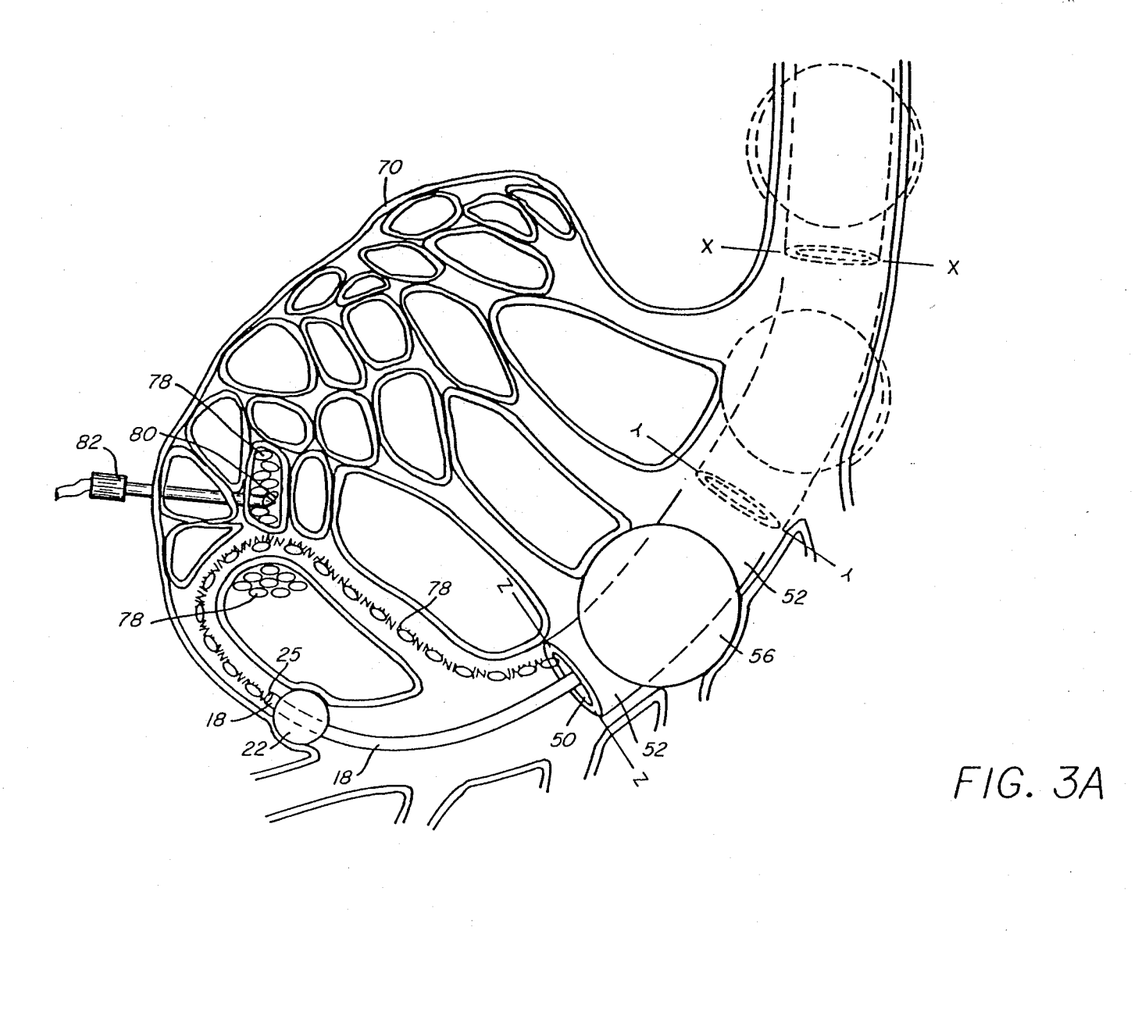

The process of improved retrograde perfusion according to the present invention is performed by inserting the infusion lumen 18 and suction lumen 52 through the patient's vein to a location near the tumor, shown in the drawings (FIG. 3, for example) as in a kidney 70. The infusion seal 22 is inflated to block the patient's vein and carrier medium is fed from container 40 at a selected flow rate by injector control 42 into the tumor through infusion lumen. The suction lumen 52 may be located very near the infusion seal 22 and suction seal 56 left uninflated during initial carrier medium injection. Alternatively, it may be moved to one of several sites in the tumor (FIGS. 3, 4 and 5) and suction seal 56 inflated.

In either situation, the flow rate of injection of carrier medium from container 40 and pressure differential between infusion lumen 18 and suction seal 56 are varied to determine potential flow paths through the tumor. Monitor 12 is then used to observe passage of carrier medium through the tumor for various flow rates, pressure differentials and lumen locations.

Figure 4:
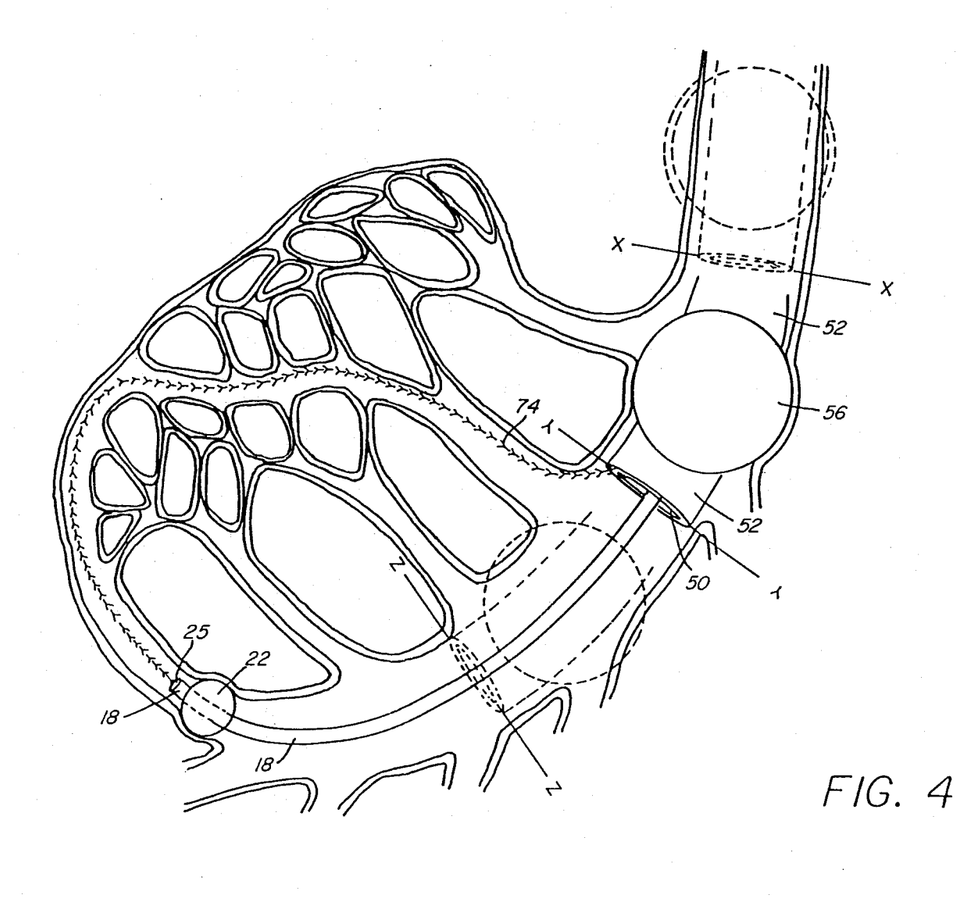

Usually, one or more flow paths (FIG. 3, 4 and 5) are formed through the kidney 70 for selected infusion conditions, indicated by flow line symbols 72 (FIG. 3), and 74 (FIG. 4). Records are kept, whether by computer or recording, of the various flow paths observed within the blood flow through the tumor. The preferential drainage can be thus determined, in effect forming a library or map of potential flow paths.

The lumens 18 and 52 are then moved into a first one of the selected infusion positions in the kidney 70 (FIG. 3) and the seals 22 and 56 inflated. A tracer fluid, such as from container 40, is then infused under control of injector control 48 at a desired flow and dosage rate and differential pressure along a first one of the preferential flow paths, as indicated by flow line symbols 72, between infusion lumen 18 and suction lumen 52 until steady state flow conditions are obtained in the catheter system C.

Once steady state flow occurs, a suitable amount of a second tracer fluid of lesser density than the first is introduced as a plug or batch, from container 44 for example, into the catheter system C as indicated by flow line symbols 78. When it is detected by the monitor 12 that the second tracer fluid reaches the site of the tumor, the fluid back pressure on the infusion stream in the catheter system C is increased by the pump 58. It should be understood that the fluid back pressure may also be increased at the infusion lumen 18, or at both lumens 18 and 52, if desired.

Since tumor blood vessels are more leaky than normal ones, the increased back pressure, however formed, forces the lower density second tracer fluid into interstitial spaces 80 of the tumor surrounding the flow path. The interstitial spaces 80 indicate a preferential target site or attack site for chemotherapeutic or other treatment of the tumor.

A record is made and kept of the preferential target area 80 so identified. Next a carrier medium, which may either be a tracer fluid from container 54 or a tracer fluid chemotherapeutic or other treatment agent from container 46, is injected into the tumor at the established flow rate and pressure along the established flow path 90 until steady state flow is determined to be present. When this occurs, a treatment agent, such as a chemotherapeutic one, which is of lesser density than the fluid then present in catheter system C, is sent from container 44 as a plug or batch through the tumor.

When it is detected that the treatment agent reaches the preferred target area 80, back pressure on the catheter system C is then increased. This forces the treatment agent 78 into the interstitial spaces at the target area 80 in the tumor, where the tumor blood vessels are more leaky than healthy blood vessels. Flow of the original carrier medium is resumed once the batch or plug of treatment again ceases. The introduction of the same or different treatment agent in plugs or batches and application of back pressure in the catheter system C can then be repeated for a suitable number of cycles according to the treatment protocol or regimen.

After the preferred target area has been established, a thermal sensor 82, such as Thermometrics Series T3000 thermistor, can be stereotaxically guided using fluoroscopy to the target site 80. Heated fluids, in the temperature ranges of about 43° C. to 45° C., may be selectively introduced for monitoring purposes as batches or plugs in the catheter system C and forced into the target area 80 using back pressure in the manner set forth above. The thermal sensor 80 can then detect the effectiveness of the therapy and monitor treatment to avoid systemic damage from the treatment.

Figure 4A:
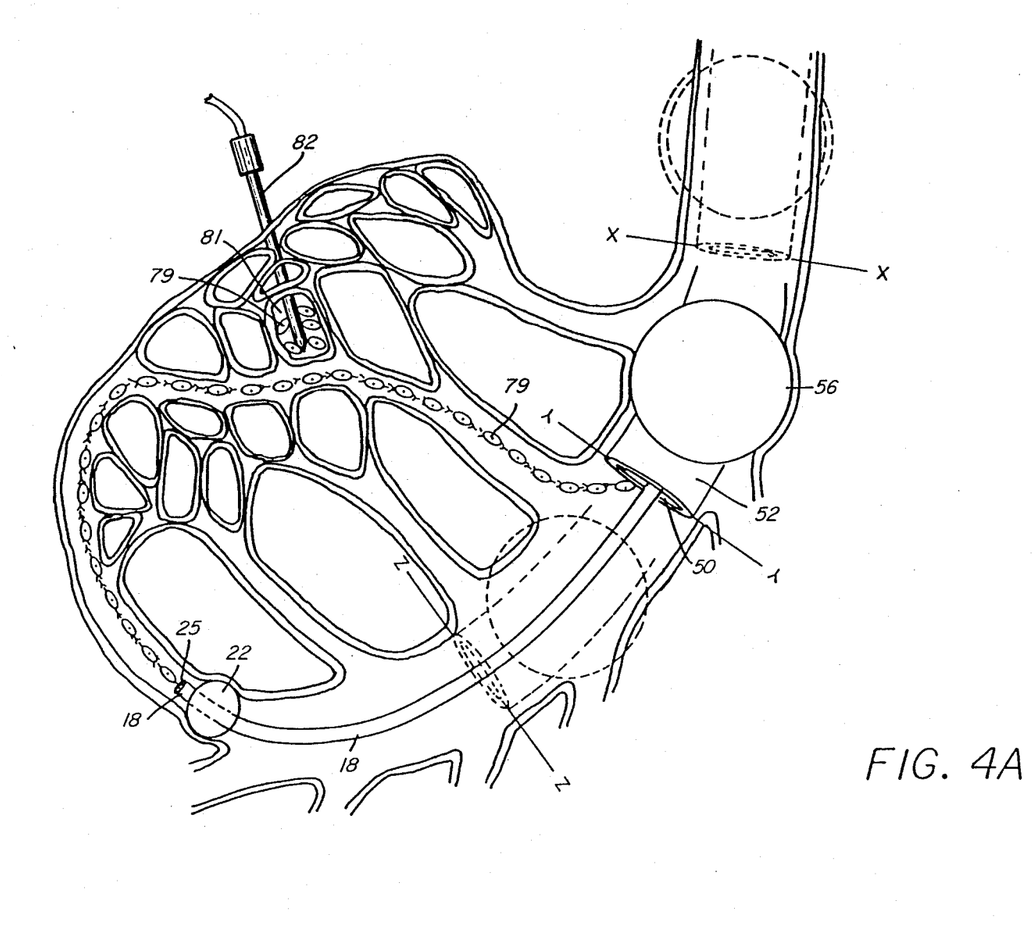

After treatment of the tumor along the first preferential flow path, the relative position of lumens 18 and 52 is then adjusted by moving the suction lumen 52 and seal 56 further away from the infusion lumen 18 and seal 22 in the tumor to a location (FIG. 4) where another preferential target site 81 along another preferential flow path through the kidney 70 was established for a particular flow rate and differential pressure. At the next location, the active ingredient from container 46, as indicated by symbols 79 (FIG. 4A) may be infused at a desired flow and dosage rate through the tumor until steady state flows is achieved. Treatment using back pressure to attack the preferred target site detected along this flow path in the foregoing manner then proceeds. Alternatively, the active ingredient from container 44 may be used again for back pressure attack at the preferred target site.

After treatment along the second flow path, lumens 18 and 52 may again be adjusted in relative position to another location where another preferential flow path was noted. Active ingredient is then infused at the noted pressures and flow and dosage rates for this flow path until steady state flow is achieved. Application of treatment agent then proceeds with back pressure in the catheter system C, using either active ingredient from container 44 or from container 46 as treatment needs indicate.

One or more of the established flow paths through the tumor may be used to infuse different active ingredients, even to a single patient, according to a treatment regimen. Alternatively, all established flow paths may be used for infusion of the same active ingredient. In this manner, the flow patterns of active ingredients through the tumor, the type of active ingredients, dosages, preferential drainage and the like may be adjusted as the progress of the treatment is noted. Separation of the tumor load from the body and formation of several preferential flow paths through the tumor in this manner creates a treatment procedure wherein the clinician may freely act upon and interact with the tumor.

The foregoing disclosure and description of the invention are illustrative and explanatory thereof, and various changes in the size, shape and materials, as well as in the details of the illustrated construction may be made without departing from the spirit of the invention.

I claim:

1. An apparatus for treating a tumor in the body of a patient with an active ingredient, comprising:
   (a) a catheter means for location in a vein of the patient near the tumor, said catheter means comprising:
      (1) a suction lumen for removing fluids; and
      (2) an infusion lumen extending beyond said suction lumen for passing fluids into the tumor;
   (b) infusion seal means on said catheter means between said infusion lumen and said suction lumen for sealing the patient's vein;
   (c) suction seal means on said catheter means for sealing the flow of fluid in the patient's vein past said suction lumen;
   (d) a source of carrier medium and a flow path injector means for injecting said carrier medium into the tumor from said infusion lumen at selected flow rates and pressures to establish preferential flow paths through the tumor;
   (e) said flow path means further comprising means for establishing a steady state flow rate and pressure in a selected one of the flow paths;
   (f) a source of a less dense carrier medium and a means for introducing said less dense carrier medium through said infusion lumen;
   (g) means for selectively increasing back pressure on the fluids in the tumor to determine a preferred target area in the tumor where said less dense carrier medium is driven into interstitial spaces in the tumor;
   (h) a source of a first fluid and an active ingredient and a treatment injector means for injecting said first fluid and thereafter said active ingredient into the patient's vein from said infusion lumen;
   (i) said means for selectively increasing back pressure further comprising means for increasing back pressure on said first fluid and active ingredient in the patient's vein when said active ingredient is at the preferred target area; and
   (j) means for collecting said first fluid and active ingredient from said suction lumen after perfusion through the tumor.

2. The apparatus of claim 1, wherein said treatment injector means further comprises:
   means for selectively injecting different active ingredients into the patient's vein from said infusion lumen so that the different active ingredients may perfuse through the tumor from the preferred target area.

3. The apparatus of claim 1, further including:
   heat sensor means for detecting temperature conditions near the tumor in the patient to monitor treatment of the patient.

4. The apparatus of claim 1, further including:
   heat sensor means for detecting temperature conditions at the preferred target area in the tumor in the patient to monitor treatment of the patient.

5. A method for treating a tumor in the body of a patient with an active ingredient, comprising the steps of:
   (a) placing a catheter having a suction lumen and an infusion lumen extending beyond the suction lumen and an infusion seal associated with the infusion lumen and a suction seal associated with the suction lumen in a vein of the patient near the tumor;
   (b) sealing the flow of fluid in the patient's vein between the infusion lumen and the suction lumen with the infusion seal;
   (c) injecting a carrier medium into the tumor from the infusion lumen at selected flow rates and pressures to establish preferential flow paths through the tumor;
   (d) sealing the flow of fluid in the patient's vein past the suction lumen with the suction seal;
   (e) injecting a carrier medium from the infusion lumen in a selected one of the established flow paths at a desired flow rate and pressure until steady state flow is established;
   (f) injecting a second, less dense carrier medium from the infusion lumen in the selected one of the established flow paths;
   (g) increasing the back pressure on the carrier medium when the second carrier medium is in the tumor to force the second carrier medium into interstitial spaces in the tumor at an attack site;
   (h) injecting an active ingredient behind a carrier fluid into the patient's vein from the infusion lumen along the established flow path;
   (i) increasing the back pressure on the carrier fluid and active ingredient when the active ingredient is at the attack site to force the active ingredient into interstitial spaces in the tumor so that the active ingredient is driven into the interstitial spaces in the tumor; and
   (j) collecting the active ingredient in the suction lumen after perfusion through the tumor.

6. The method of claim 5, further including the steps of:

repeating said steps of injecting an active ingredient and increasing the back pressure on the carrier fluid and active ingredient.

7. The method of claim 5, further including the steps of:
   (a) selectively injecting different active ingredients behind the carrier fluid; and
   (b) increasing the back pressure when the different active ingredients are at the attack site so that the different active ingredients are driven into the tumor.

8. The method of claim 5, further including the steps of:
   (a) changing the flow rate and pressure of the carrier medium to a new value to establish a different flow path through the tumor;
   (b) maintaining the flow rate and pressure at the new valve until steady state flow is established in the different flow path;
   (c) injecting a second, less dense carrier medium from the infusion lumen in the different flow path;
   (d) increasing the back pressure on the carrier medium when the second carrier medium is in the tumor to force the second carrier medium into interstitial spaces in the tumor at an attack site in the different flow path;
   (e) injecting an active ingredient behind a carrier fluid into the patient's vein from the infusion lumen along the different flow path;
   (f) increasing the back pressure on the carrier fluid and active ingredient when the active ingredient is at the attack site to force the active ingredient into interstitial spaces in the different flow path in the tumor so that the active ingredient is driven into the interstitial spaces in the different flow path in the tumor.

9. The method of claim 5, further including the step of:

monitoring temperature conditions in the tumor.

10. The method of claim 5, further including the steps of:
    (a) injecting a heated fluid behind the carrier fluid into the patient's vein from the infusion lumen along the established flow path;
    (b) increasing the back pressure on the carrier fluid and heated fluid when the heated fluid is at the attack site to force the heated fluid into interstitial spaces in the tumor so that the heated fluid is driven into the interstitial spaces in the tumor.

11. The method of claim 10, further including the step of:

monitoring temperature conditions at the attack site in the tumor.

* * * * *